US011058405B2

(12) United States Patent
Knowles et al.

(10) Patent No.: US 11,058,405 B2
(45) Date of Patent: Jul. 13, 2021

(54) SURGICAL TOOL

(71) Applicant: Queen Mary University of London, London (GB)

(72) Inventors: Charles Henry Knowles, London (GB); Robin Kenneth Stewart Phillips, Middlesex (GB)

(73) Assignee: Queen Mary University of London, London (GB)

( * ) Notice: Subject to any disclaimer, the term of this patent is extended or adjusted under 35 U.S.C. 154(b) by 235 days.

(21) Appl. No.: 16/319,058

(22) PCT Filed: Jun. 13, 2017

(86) PCT No.: PCT/EP2017/064452
§ 371 (c)(1),
(2) Date: Jan. 18, 2019

(87) PCT Pub. No.: WO2018/015073
PCT Pub. Date: Jan. 25, 2018

(65) Prior Publication Data
US 2020/0245985 A1    Aug. 6, 2020

(30) Foreign Application Priority Data

Jul. 20, 2016 (GB) ..................... 1612599

(51) Int. Cl.
*A61B 17/00* (2006.01)
(52) U.S. Cl.
CPC .. *A61B 17/0057* (2013.01); *A61B 2017/0046* (2013.01); *A61B 2017/00641* (2013.01); *A61B 2217/007* (2013.01)

(58) Field of Classification Search
CPC .... A61F 9/0017; A61F 9/007; A61F 9/00781; A61B 17/0057; A61B 2017/0046; A61B 2017/00641
See application file for complete search history.

(56) References Cited

U.S. PATENT DOCUMENTS 9,907,885 B2 * 3/2018 Keighley ............... A61L 31/06
2007/0031508 A1 * 2/2007 Armstrong .............. A61L 27/24
424/572

(Continued)

FOREIGN PATENT DOCUMENTS

CN       2362498 Y    9/2000
CN      201094797 Y   8/2008
(Continued)

OTHER PUBLICATIONS

Lunniss et al., The Lancet, vol. 340, dated Aug. 15, 1992, pp. 394-396.

(Continued)

*Primary Examiner* — Ashley L Fishback
(74) *Attorney, Agent, or Firm* — Adsero IP

(57) ABSTRACT

A surgical tool for use in the treatment of anal fistulas includes an elongate, flexible probe having a channel running there through; a seton attached to a proximal end of the probe; and a wire located within the channel, and movable along the channel; wherein: the probe has a first stiffness and the wire has a second stiffness, the first stiffness being less than the second stiffness.

25 Claims, 15 Drawing Sheets

(56) References Cited

U.S. PATENT DOCUMENTS

| | | | |
|---|---|---|---|
| 2007/0129757 A1* | 6/2007 | Armstrong | A61M 5/007 606/213 |
| 2008/0051831 A1* | 2/2008 | Deal | A61B 17/12099 606/213 |
| 2008/0245374 A1 | 10/2008 | Agnew | |
| 2014/0227337 A1 | 8/2014 | Keighley | |
| 2015/0250460 A1 | 9/2015 | Horeman et al. | |
| 2015/0335860 A1* | 11/2015 | Klocke | A61M 25/0067 604/510 |

FOREIGN PATENT DOCUMENTS

| | | |
|---|---|---|
| CN | 202526154 U | 11/2012 |
| CN | 203693660 U | 7/2014 |
| EP | 2926740 | 3/2015 |
| WO | WO-2005-020823 | 3/2005 |
| WO | WO-2005-020823 A1 | 3/2005 |
| WO | WO-2005-096957 | 10/2005 |
| WO | WO-2011-151659 A2 | 8/2011 |
| WO | WO-2014-023962 A2 | 2/2014 |
| WO | WO-2016-189107 A1 | 12/2016 |

OTHER PUBLICATIONS

Williams et al., The Treatment of Anal Fistula: ACPGBI Position Statement, 2007, 33 pages.

Sagar et al., Surgery of the Anus, Rectum and Colon, Keighley & Williams 4$^{th}$ Edition, vol. 1, 3 pages.

Ho et al., Randomized Controlled Trial of Primary Fistulotomy with Drainage Alone for Perianal Abscesses, British Library, 4 pages.

Westerterp et al., Anal Fistulotomy Between Skylla and Charybdis, dated Dec. 20, 2002, 3 pages.

Lindsey et al., A Ranomized, Controlled Trial of Fibrin Glue vs. Conventional Treatment for Anal Fistula, British Library, vol. 45, No. 12, 8 pages.

Singer et al., Treatment of Fistulas-in-Ano with Fibrin Sealant in Combination with Intra-Adhesive Antibiotics and/or Surgical Closure of the Internal Fistula Opening, British Library, Apr. 2005, 10 pages.

Johnson et al., Efficacy of Anal Fistula Plug vs. Fibrin Glue in Closure of Anorectal Fistulas, British Library, Mar. 2006, 6 pages.

Shanwani et al., Ligation of the Intersphincteric Fistula Tract, Diseases of the Colon & Rectum, vol. 53:1, 2010, 4 pages.

Parks et al., Symposium Fistula-in-Ano, Diseases of the Colon & Rectum, vol. 19:6, 1976, 13 pages.

Ramanujam et al., The Role of Seton in Fistulotomy of the Anus, Surgery, Gynecology & Obstetrics, 1983, vol. 157, 4 pages.

Williams et al., Recurrence of Crohn's Disease after Resection, Br. J. Surg., 1991, vol. 78, 10 pages.

Lentner et al., Long-Term Indwelling Setons for Low Transsphincteric and Intersphincteric Anal Fistulas, Diseases of the Colon & Rectum, Oct. 1996, 5 pages.

Miles, Corman, Classic Articles in Colonic and Recal Surgery, Diseases of the Colon & Rectum, Apr. 1980, 4 pages.

Lockhart-Mummery, J.P., Discussion on Fistula-in-Ano, Surg., Sur. Sect. Proct., May 1929, 28 pages.

Riordan et al., A Systematic Review of the Anal Fistula Plug for Patients with Crohn's and Non-Crohn's Related Fistula-in-Ano, Diseases of the Colon & Rectum, 2012, 8 pages.

Morson et al., Anal Lesions in Crohn's Disease, The Lancet, Dec. 1959, 2 pages.

White, et al., Seton Management of Complex Anorectal Fistulas in Patients with Crohn's Disease, Diseases of the Colon & Rectum, Jul. 1990, 3 pages.

Zanotti et al., An Assessment of the Incidence of Fistula-in-ano in four countries of the European Union, Springer-Verlag, 2007, 4 pages.

Ozuner et al., Long-Term Analysis of the Use of Transanal Rectal Advancement Flaps for Complicated Anorectal/Vaginal Fistulas, Diseases of the Colon & Rectum, Jan. 1996, 5 pages.

Neotherix, Seton, JPG.

Neotherix Seton Scaffolding, University of Birmingham, Project Highlights, JPG.

International Search Report, GB1612599.9, dated Jan. 10, 2017, 4 pages.

International Search Report & Written Opinion, PCT International Application No. PCT/EP2017/064452, filed on Jun. 13, 2017, 21 pages.

\* cited by examiner

SURGICAL TOOL

RELATED APPLICATIONS

This application is a 35 U.S.C. § 371 national phase application of PCT/EP2017/064452 (WO 2018/015073) filed on Jun. 13, 2017, entitled "Surgical Tool", which is a PCT application of GB-1612599.9 filed on Jul. 20, 2016, which is incorporated herein by reference in its entirety.

TECHNICAL FIELD OF THE INVENTION

This invention relates to a surgical tool which may be used in the treatment of anal fistulas, a seton forming part of the surgical tool, and a method of forming the seton.

BACKGROUND TO THE INVENTION

Anorectal sepsis is a very common presentation in hospitals, which may present itself as a fistula. A fistula consists of a primary tract which passes from an internal opening in the anal canal to an external opening in the perineum. In more complex cases, secondary tracts may branch from the primary tract. Pain and pus discharge from the external opening can cause great discomfort to a patient. Following clinical and radiological assessment, effective treatment almost always requires surgery, the success of which requires eradication of the primary tract. In many patients, this is achieved by laying open the fistula in a process known as a fistulotomy. However, in many cases, a fistulotomy may lead to a disturbance of continence due to division of the sphincter muscle. Despite advances in biological glues and plugs to seal or block the primary tract, or new methods to ligate it, the mainstay of these procedures is still to use a loose seton to effect controlled drainage along the tract, prevent further exacerbations of anal sepsis and to allow healing of secondary tracts (Parks & Stitz, 1976[1]; Ramanujam et al., 1983[2]; Williams et al., 1991[3]; Lentner et al., 1996[4]). Known loose setons employ a thick, synthetic non-absorbable suture material such as polyester e.g. Ethibond, which is passed through the primary tract from the external opening to the internal opening, where it is retrieved and drawn out of the anal canal and loosely tied.

FIGS. 2A and 2B show "before" and "after" images of the insertion of a seton into a fistula adjacent to an intersphincteric abscess. The process generally involves the following steps: firstly, the perineum is examined to delineate the pathoanatomy, then hydrogen peroxide ($H_2O_2$) is injected into the external opening of the fistula tract to help to identify the internal opening; a fistula probe is passed along the fistula tract, and a seton is threaded through an eye at the end of the fistula probe, or advanced along a groove in the probe, and the probe is then withdrawn from the tract. Finally the ends of the seton are knotted to prevent loss. For the majority of cases, these steps are readily possible, though cumbersome, with surgical experience and expertise. However, in patients with long, high or angulated fistula tracts, this procedure can be problematic, especially in relation to identification of the internal opening and passing of the probe through the tract. A relatively rigid fistula probe must negotiate the long angulated track, and also pass through the frequently occurring hour-glass deformity (shown in FIG. 3). Furthermore, the nylon may either be impassable or difficult to locate and retrieve deep in the anal canal.

FIG. 1 shows some instruments currently used in the process as described above. The lachrymal probes are narrow in diameter and may easily pass through the hourglass deformity, thus delineating the anatomy of the fistula. However, these do not facilitate subsequent passage of the seton for which Lockhart-Mummery fistula probes are required. These probes, also shown in FIG. 1 have been in use, virtually unchanged, since the early 1900s.

SUMMARY OF THE INVENTION

In order to address the problems set out above, at its most general, the present invention provides a disposable surgical tool for use in the treatment of anal fistulas the tool including, amongst other features a probe shaft and a seton attached to a proximal end of the probe shaft, the tool arranged to result in simple seton deployment. Such an arrangement allows a reduction in operation times, and a reduction in potential iatrogenic trauma to the anal canal, and also obviates the need (and therefore costs) of instrument sterilization, and furthermore obviates the need for multiple instruments, as is the current practice described above.

Throughout this text, the terms "proximal" and "proximal end" are used to describe an end of a particular feature which is located at the end closest to the surgeon during the procedure as outlined above. Similarly, the terms "distal" and "distal end" are used to describe the end of a particular feature which is located furthest away from the surgeon's hand during the procedure as outlined above. For example, the proximal end of the fistula tract corresponds to the external opening, and the distal end of the fistula tract corresponds to the internal opening. The term "seton" is well-known in this technical field, and may refer to any length of thread, cord or the like which is used to hold the walls of the fistula open, thus allowing any fluids in the fistula to drain continuously during healing.

In particular, a first aspect of the present invention provides a surgical tool for use in the treatment of anal fistulas, the tool including:
 an elongate, flexible probe having a channel running therethrough;
 a seton attached to a proximal end of the probe;
 a wire located within the channel, and movable along the channel;
 wherein:
  the probe has a first stiffness and the wire has a second stiffness, the first stiffness being less than the second stiffness.

Optional features of the present invention are set out below. These optional features may apply singly or in any combination with any aspect of the present invention.

Such an arrangement provides a surgical tool which has a variable stiffness.

More specifically, in use in a procedure as outlined above, the probe may be inserted into an external opening of the fistula tract with the wire in place in the channel. In this configuration the probe has a stiffness which is required to navigate the tract and reach the internal opening, which is especially advantageous in the cases of tortuous or narrow tracts. Once a distal end of the probe has been located at the internal opening, i.e. in the anal canal, the wire can be retracted through the channel, leaving only the hollow probe in place, which has a lower stiffness, i.e. is more flexible than the probe with the wire in place. Then, by drawing the flexible probe through the internal opening of the fistula tract, the seton, whilst still attached to the probe may be drawn through the entirety of the tract with ease, using the probe. Thus, it is preferable that as well as being movable within the channel, the wire is fully retractable from the channel. The term "retractable" here refers to the case where the wire may be completely removed from the channel, preferably at its proximal end. To prevent injury or damage to the patient during insertion of the probe, the distal end of the probe is preferably rounded in shape, for example hemispherical. In particular, the end of the wire is preferably neither exposed nor exposable from the distal end of the probe.

In a preferred embodiment, the seton may be swaged to the proximal end of the probe. In which case, when the seton has been drawn all the way through the fistula tract, the probe may be cut off and discarded, and the two ends of the seton joined to form a loop. In alternative embodiments the seton may be attached to the probe shaft by adhesive bonding, solvent bonding, fusion bonding, ultrasonic welding, heat welding, induction welding, vibration welding, hot gas welding, mechanical fastening, or friction fitting.

The probe is preferably formed of a flexible polymer material. In preferred embodiments, the probe may include a polyurethane-based material, such as extended isoplast 2530 TPU. The probe, and indeed all other components of the surgical tool may me made from a range of polymers and metals. Such materials are preferably certified for medical use, and suitable for sterilization, e.g. using ethylene oxide.

The outer diameter of the probe is preferably no more than 5 mm, and more preferably no more than 2 mm, and even more preferably no more than 1.5 mm and most preferably no more than 1.2 mm. A narrow probe such as this keeps to a minimum patient discomfort, and allows easier negotiation of the tract during insertion of the probe. The length of the probe may be no less than 3 cm, and may be no more than 20 cm.

At least a distal end of the probe preferably includes a photoluminescent, or "glow in the dark" material so that the end of the probe is easily identified when emerging from the internal opening, which may be located deep inside the anal canal. In this application, the term photoluminescent is used to refer to materials which emit light in response to stimulation by e.g. visible light or UV light, but which do not retain their glow once the stimulating light ceases to be incident upon the material. "Glow-in-the-dark" materials are similar to photoluminescent materials, except they retain their glow after the stimulating light ceases to be incident upon the material. The photoluminescent or glow-in-the-dark materials may either form a coating on the probe, or they may be incorporated into the material making up the bulk of the probe.

The probe preferably includes a handle. The handle is preferably located at or near the proximal end of the probe, and is preferably attached thereto. The handle allows a surgeon to grip the probe in place while retracting the wire from the channel of the probe, and helps to manipulate the probe along the tract. In preferred embodiments, the position of the handle on the probe shaft is adjustable, or in other words, the handle is movable along the probe, and preferably also includes a locking mechanism for locking the handle into a selected position along the probe. This enables a surgeon to change the position at which the probe may be gripped depending on the length of the probe which is necessary for a given procedure.

The handle may include a guide, through which the probe may pass when the handle is located on the probe. In order to lock the handle into place on the probe, the handle may include a locking mechanism. In one embodiment the locking mechanism may include an actuation means which is movable between a locked position and an unlocked position. For example, when the actuation means is moved from an unlocked to a locked position, this may cause the guide to narrow (e.g. the walls may move closer together), and thus grip the probe tightly enough that the handle is no longer able to move up and down the guide. The actuation means may be in the form of a tab which is slidable relative to the rest of the handle between a first, locked, position and a second, open, position.

The handle may include a gripping portion, which may have a ridged surface to increase grip, thus improving the degree of control with which the handle may be moved, either along the probe, or in order to navigate the full length of the fistula tract. In preferred embodiments, the gripping portion may also function as the sliding tab described in the preceding paragraph. In order to impart the best gripping function, the ridges on the surface of the gripping portion/sliding tab are therefore preferably aligned in a direction perpendicular to, or substantially perpendicular to the direction of movement of the tab.

In preferred embodiments, the handle may be removable, or in other words the handle may be removably attached to the probe. Thus, after the internal opening of the fistula tract has been located, the handle may be removed, and then the probe and seton may be drawn through the tract until the seton has emerged from the internal opening for joining up. The handle may be removable from a proximal end of the seton, by sliding all the way along the length of the seton. Alternatively, the handle may include two cooperating parts, which when engaged with each other, cause the handle to be attached to the probe. For example, the handle may be in the form of a clip. The handle may then be disposed of, or in other embodiments, the handle may be sterilized and reused. The handle is preferably made of a polymer based material, e.g. polyethylene, polypropylene, polystyrene, polyester, polycarbonate, polyvinyl chloride, polyethersulfone, polyacrylate, polysulfone, polyetheretherketone, fluoropolymers, or polyamide. Broadly speaking the handle preferably has a high tensile strength, is preferably formed from a material which is easily injection-moulded and machined. It is also preferable that the handle allows a good grip on the probe shaft, and that it does not absorb water, in order to prevent expansion and therefore friction with the wire.

The wire preferably includes a handle portion, preferably located at or near its proximal end. This improves the control with which the wire may be gripped during retraction and insertion of the wire into the channel of the probe. Furthermore, a handle portion improves the ease with which the wire may be rotated within the channel to navigate the fistula tract. The handle portion may be a portion of the proximal end of the wire which is curved back on itself to form a loop at the end. In other embodiments, the handle portion may include a tab portion either integral with or attached at or near the proximal end of the wire.

Furthermore, the wire (preferably its distal end) may have a curved shape. In some embodiments the wire may be deformable or malleable, e.g. plastically deformable, so that before insertion of the probe through the fistula tract, the surgeon may bend the wire into an appropriate shape to allow greatest ease of the passing of the wire from the external to the internal opening. In those embodiments, the wire is preferably rigid enough to hold its shape while being passed through the fistula tract. In alternative embodiments, the wire may be "pre-bent" into a desired curved shape, and stiff enough not to deform during use.

The wire is preferably rigid, with a relatively high tensile strength, and malleable.

In some embodiments, which may be referred to herein as "multi-wire" structures, the surgical tool may include a first wire, having the second stiffness (e.g. as described above) and a second wire having a third stiffness. The first and second wires may be identical or substantially identical, and in particular the second stiffness may be equal or substantially equal to the third stiffness. However, in other embodiments, the second stiffness may be greater than or less than the third stiffness. The optional features of the first wire which are set out above may also apply equivalently to the second wire, and for conciseness are not repeated here.

In preferred embodiments, the probe includes a first channel in which the first wire is located, and a second channel in which the second wire is located. The first and second wires are preferably movable along the first and second channels respectively, and more preferably, are movable relative to each other. In this way, the stiffness of a given region of the probe is adjustable between three stiffnesses: a stiffness when both the first and second wired are located in their respective channels at that point along the wire, a stiffness when only one of the first and second wires is located in its respective channel at point along the wire, and a stiffness when neither of the wires is located in its respective channel at that point along the wire. This enables greater control of the wire during the insertion process.

In embodiments having only a single channel in the probe, the maximum outer diameter of said channel is preferably no more than 2.5 mm, and more preferably no more than 1.5 mm, and even more preferably no more than 1 mm, and most preferably no more than 0.8 mm. In embodiments having a first channel and a second channel, the diameter of each or both channels is preferably no more than 2 mm, and more preferably no more than 1 mm, and most preferably no more than 0.75 mm.

The wires may have a circular cross section. However, in other preferred embodiments, the wires may have a non-circular cross section. More specifically, the channels and the wires are shaped such that rotation of the wire about its longitudinal axis causes a portion of the wire to engage with an inner surface of the channel, to cause corresponding rotation of the probe itself. In this way, when the wire is twisted (e.g. using a handle portion), rather than the wire simply rotating within the channel, a torque may be exerted on the probe, causing the probe to rotate in order to navigate the fistula tract. In other words, the torsional stability of the probe is improved. This may be especially advantageous in cases of particularly tortuous tracts. The cross-section of the wire may, for example, be elliptical, square or rectangular. In preferred embodiments, however, the wires may have D-shaped or semi-circular cross sections, and the channels may have corresponding D-shaped or semi-circular cross sections. In preferred embodiments, in cross section, the straight edges of the D-shaped or semi-circular channels are facing each other, and the curved edges are located towards the outer edge of the probe. Thus, the probe itself may have a circular or substantially circular cross section.

In addition to a first channel (and a second channel, in embodiments where it is included), the probe may also include a liquid delivery channel, which is arranged to deliver a liquid from a proximal end e.g. from a syringe or the like, to a distal end of the probe. Accordingly, the liquid delivery channel preferably terminates in an aperture at or near to the distal end of the probe. In use, the liquid delivery channel may be used for the delivery of hydrogen peroxide or the like, in order to identify the internal opening of the fistula tract when the probe is passed through. Hydrogen peroxide is used since it foams at the internal opening of the fistula and is easier to see than simple dyes. Fluorescent dyes may also be used. The liquid delivery channel may be located between the first and second channels. The liquid delivery channel may have the same dimensions as the first channel and/or the second channel, i.e. the liquid channel may have a maximum outer diameter of no more than 2 mm, and more preferably no more than 1 mm, and most preferably no more than 0.75 mm.

The seton itself may include any of the following features set out below.

A primary function of the seton, the ends of which are joined and which is left inside the patient after surgery, is to allow the draining of fluids which may build up in the fistula tract. Thus, it is preferable that the seton does not plug the fistula tract, or in other words, that the shape of the cross section of the seton is selected such that not all of the outer surface of the seton is in contact with the inner surface of the fistula tract, when the seton is in place inside the fistula tract. Preferably, when the seton is in place inside the fistula tract, there are channels formed between the outer surface of the seton and the inner surface of the fistula tract which allow fluid to flow out of the fistula tract, i.e. to ensure constant drainage is possible. There are a number of differently shaped cross sections which the seton may have in order to achieve this. In all cases, it is preferable that the cross section of the seton has no sharp edges, and that all corners or vertices are rounded or bevelled.

In preferred embodiments, the seton preferably has a maximum outer diameter of 5 mm, and preferably no more than 3 mm.

In one embodiment the cross section of the seton may be circular, substantially circular, elliptical or substantially elliptical, with a cutout portion. The cross-section may have a plurality of cutout portions. In this embodiment, on the assumption that the fistula tract has a substantially circular cross section, the circular/elliptical portion of the perimeter of the cross section may be in contact with the wall of the fistula tract, but there will be a gap (i.e. a channel) defined between the outer surface of the cutout portion and the wall of the fistula tract. In preferred embodiments there may be more than one cutout portion, for example, there may be two, three, or four cutout portions. In preferred embodiments having multiple cutout portions, it is preferable that the cutout portions are evenly distributed circumferentially around the cross section of the seton.

In alternative, but similar embodiments to those described in the previous paragraph, the cross section may include a plurality of radial arms extending from the centre to an outer edge of the cross section. For example, there may be three arms distributed circumferentially evenly, to resemble a wind turbine, or four arms arranged in a cross shape. Rather than being straight, the arms may be lobe-shaped, i.e. the cross section of the seton may include a plurality of radial lobes to give the cross section of the seton a flower-like, clover-like, club-like, or shamrock-like appearance. These cross-sections are described in more detail later in the application, where they may be understood better with reference to FIGS. 11A to 11K. In each of the above-described cases, in use, a number of channels may be defined between the outer surface of the seton and the wall of the fistula tract. Alternatively, the seton may be helical, in which case, when in place, built-up fluid within the fluid would be able to drain from a helical channel, e.g. as with an Archimedes screw.

The seton preferably comprises a polymer based material for improved comfort. For example, the seton may comprise a polyurethane based compound, such as extruded carbothane aliphatic TPU. The material from which the seton is made preferably exhibits one or more of the following properties: suppleness, flexibility, high tensile strength, elasticity, shape memory, kinking resistance, torque resistance, low coefficient of friction, pressure resistance, ease of welding, ease of bonding, ease of extruding. Accordingly, the seton may be produced either by extrusion, or by injection moulding.

A key part of the procedure in which the surgical tool of the present invention may be employed, is the joining of the two ends of the seton (i.e. one at the internal opening, and one at the external opening) to form a loose loop, after the seton has been drawn through the fistula tract. With known setons, the ends are usually secured together by knotting. However, many patients find the knot to be a source of great irritation, particularly when in a seated position. Thus it is highly desirable to produce a knotless, low-profile or seamless join between the two ends. In preferred embodiments of the present invention, this is best achieved by providing a seton which has cooperating proximal and distal ends. More specifically one end of the seton may include a recess, configured to receive, mate with or cooperate with the other end of the seton, or alternatively a projection which is disposed on said other end.

In embodiments in which the distal end of the seton is attached e.g. by swaging to the proximal end of the probe, the seton must be cut to detach it from the probe. So, where the recess is to be located at the distal end of the seton, the seton may have a hollow portion at a cutting portion (i.e. a length of the seton which should be cut to detach it from the probe) located at or near the distal end. When the hollow portion is cut into, the recess is then exposed. For ease of manufacture however, it is preferable that the recess is located at the (free) proximal end, and that the recess is configured to receive, mate with or cooperate with the distal end of the seton, in particular the distal end of the seton arising as a result of the cut.

In some embodiments, in order to ensure a secure join between the distal and proximal ends of the seton, one or both of the proximal and the distal end may include an adhesive, and preferably a UV-curing adhesive, which may be cured using a UV torch or the like after the ends are joined. Adhesives such as Superglue, e.g. Loctite cyanoacrylates (which are medical grade tested to ISO 10993). Heat-sealing or suturing may also be used to bind the two ends.

The optional features set out above may all apply, singly or in combination with the following additional aspects of the invention set out below, where compatible. In addition, the features of the first aspect of the invention may also be combined with the features of the additional aspects of the invention below.

A second aspect of the invention provides a surgical tool for treatment of anal fistulas, the tool including:
 a flexible, elongate probe;
 a seton attached to a proximal end of the probe;
 a handle removably attached to the probe.

A third aspect of the invention provides a surgical tool for treatment of anal fistulas, the tool including:
 a flexible, elongate probe;
 a seton attached to a proximal end of the probe;
 wherein either:
  (a) a cross section of the seton is circular, elliptical, substantially circular or substantially elliptical and includes a cutout portion;
  (b) a cross section of the seton includes a plurality of radial arms;
  (c) a cross section of the seton includes a plurality of radial lobes; or
  (d) a cross section of the seton is flower-shaped, clover-shaped, club-shaped or shamrock-shaped
  (e) the seton is helical.

A fourth aspect of the present invention provides a seton for attachment to a surgical tool for treatment of anal fistulas, wherein either:
 (a) a cross section of the seton is circular, elliptical, substantially circular or substantially elliptical and includes a cutout portion;
 (b) a cross section of the seton includes a plurality of radial arms;
 (c) a cross section of the seton includes a plurality of radial lobes; or
 (d) a cross section of the seton is flower-shaped, clover-shaped, club-shaped or shamrock-shaped
 (e) the seton is helical.

A fifth aspect of the invention provides a method of forming a seton according to the fourth aspect of the invention which includes at least one of an extrusion step and an injection moulding step.

Further optional features of the invention are set out below.

BRIEF DESCRIPTION OF THE DRAWINGS

Embodiments of the invention will now be described with reference to the drawings, in which:

FIGS. 11A to 11K show cross-sections of various setons which may be used in embodiments of the present invention.

DETAILED DESCRIPTION OF THE DRAWINGS

Figure 1:
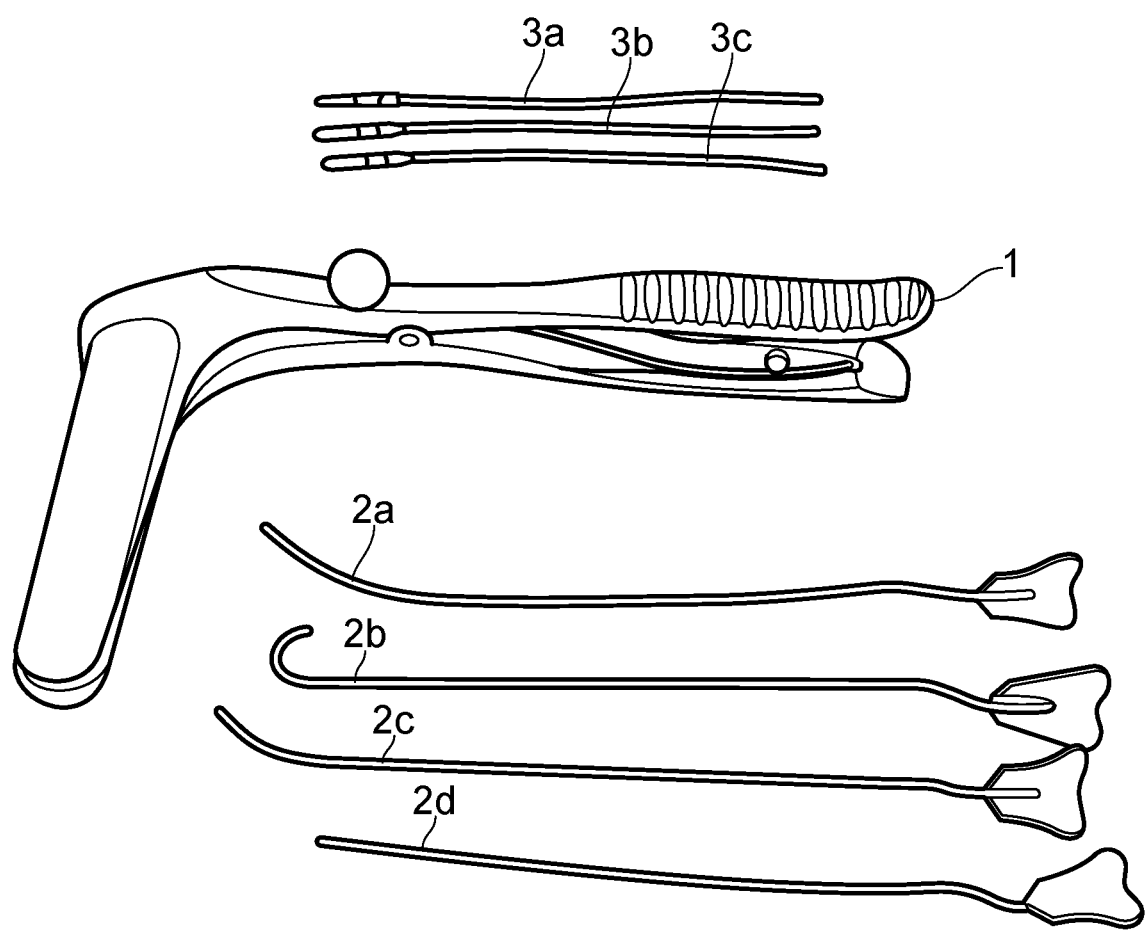
FIG. 1 shows a selection of surgical instruments used in the deployment of setons for the treatment of anal fistulas.

FIG. 1 shows a selection of known instruments used in the deployment of setons into anal fistulas. The Eisenhammer anal retractor 1 is used to open up the anus during the procedure. Before the seton is pass into the fistula, a probe must be passed through to establish the location of the internal opening of the fistula tract within the anal canal. Lockhart-Mummery fistula probes 2a-d may be used for this purpose, and indeed have been used since the early 1900s. As is shown in FIG. 1, the Lockhart-Mummery probes 2a-d may be provided with an array of differently shaped ends, depending on the geometry of the fistula itself; they have limited malleability (varies slightly between probes). An alternative to the Lockhart-Mummery probes 2a-d are lacrimal probes 3a-c, which have a narrower diameter, which can make it easier to navigate narrow fistulas, or hourglass deformities (see e.g. FIG. 3). Unlike Lockhart-Mummery probes, lacrimal probes 3a-c are easily malleable, so can be bent into a desired shape before insertion into the fistula tract. As will be clear, none of the instruments 1, 2, 3 as shown in FIG. 1 includes an attachment point for a seton, nor do they show an attached seton, retractable wires, or an injection channel.

Figure 2A:
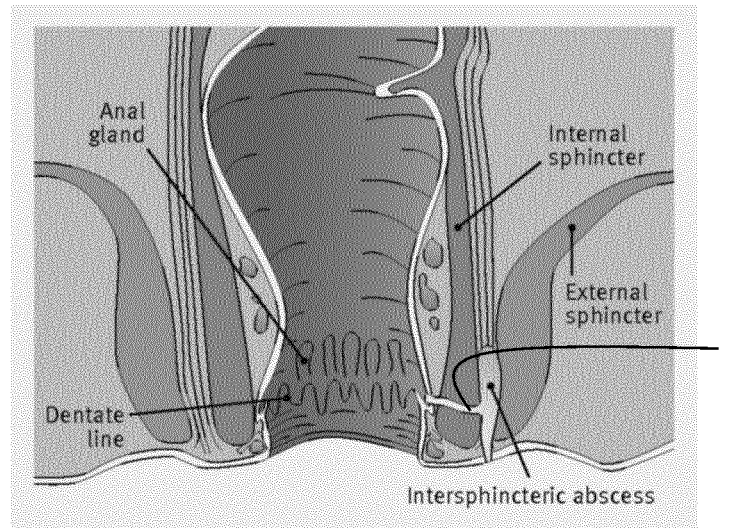
FIGS. 2A and 2B shows a coronal cross section of region surrounding the anal canal, and also showing an intersphincteric abscess and a fistula with a seton in place.
Figure 2B:
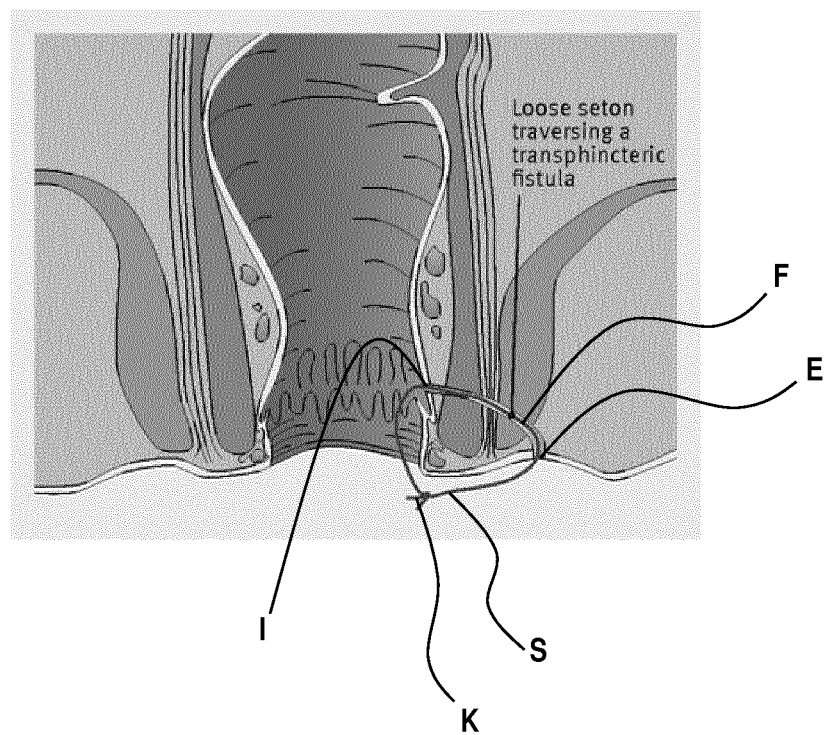
Figure 3:
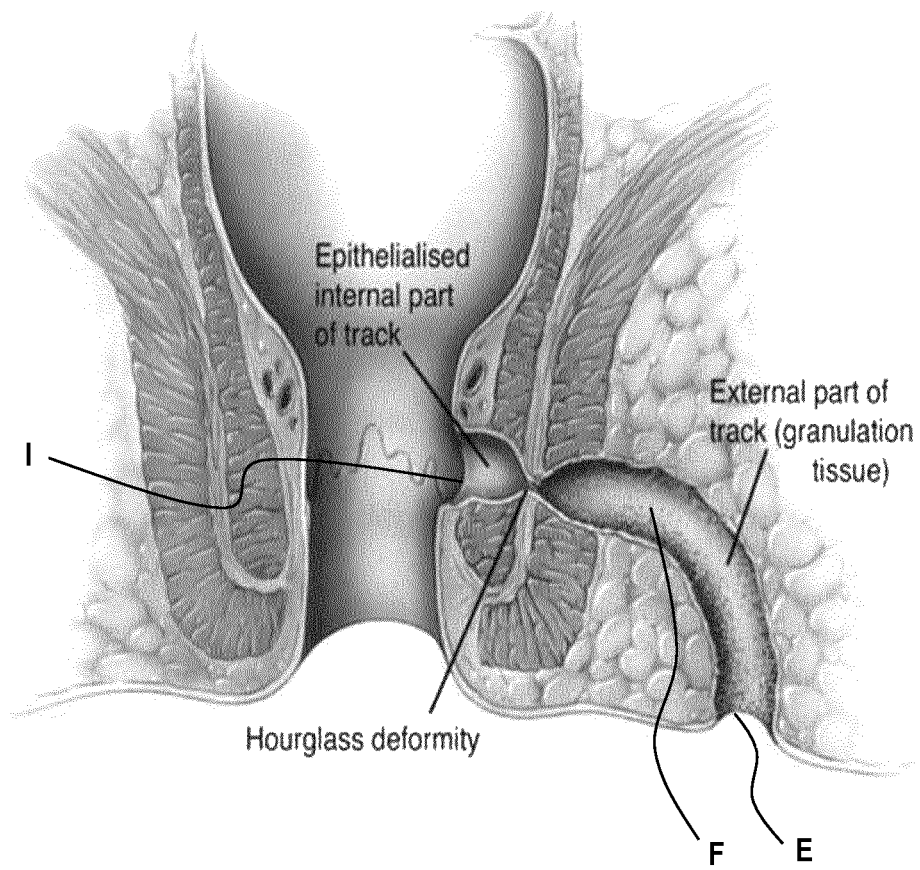
FIG. 3 shows another coronal cross section of the region surrounding the anal canal, including an hourglass deformity in the fistula tract.

FIGS. 2A and 2B are schematic diagrams showing the anatomy of the area of interest. In FIG. 2A, an intersphincteric abscess is located between the internal and external sphincter muscles, which contains an accumulation of fluids such as pus, within a fistula tract F. Such an accumulation of fluid can lead to discomfort and discharge for the patient. Therefore, it is desirable to drain the fluid from the fistula tract F. FIG. 2B shows a fistula tract F' (having an internal opening I and an external opening E) with a seton S in place. The ends of the seton S are tied together in a knot K, which as mentioned above can also lead to discomfort when the patient is in a sitting position. Having the seton S in place allows the accumulated fluid to drain continuously. FIG. 3 shows an example of the hourglass deformity, again in a coronal plane, in which fistula tract F has a narrow portion between the internal opening I and the external opening E. This part may be particularly difficult to navigate using Lockhart-Mummery probes 2a-d as shown in FIG. 1.

Figure 4:
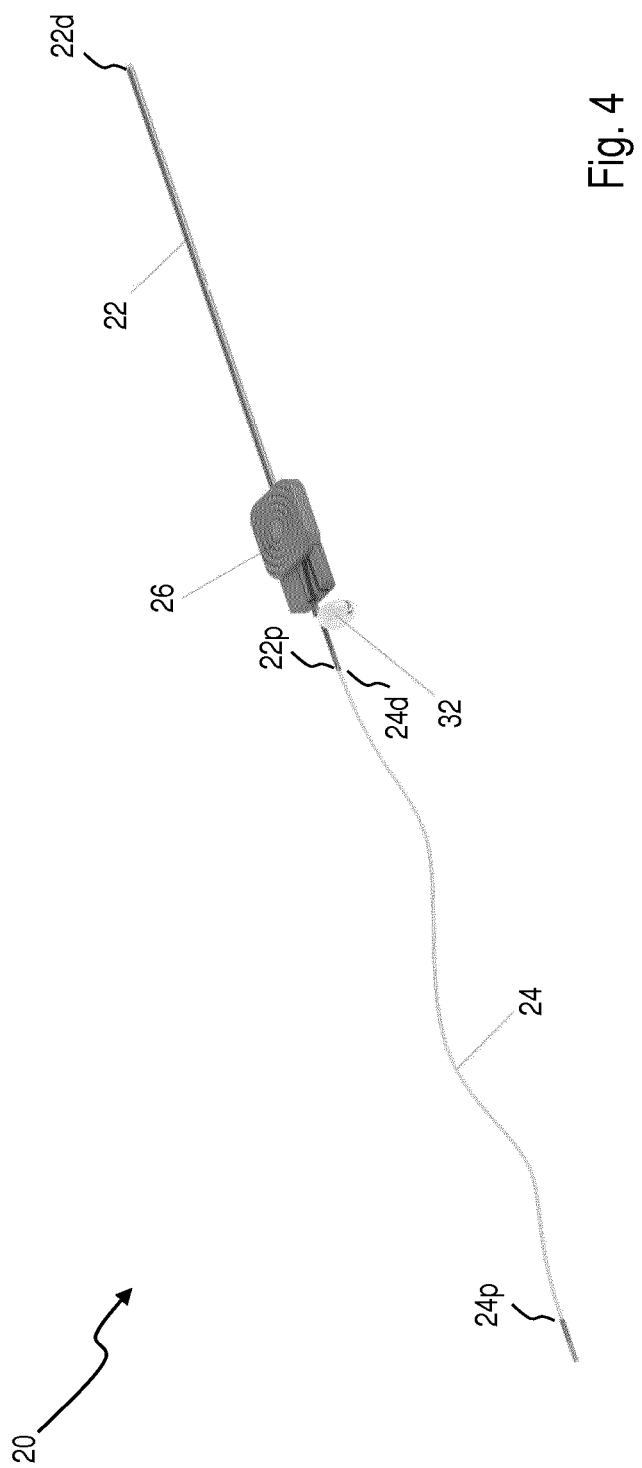
FIG. 4 shows a perspective view of a surgical tool according to an embodiment of the present invention.
Figure 5A:
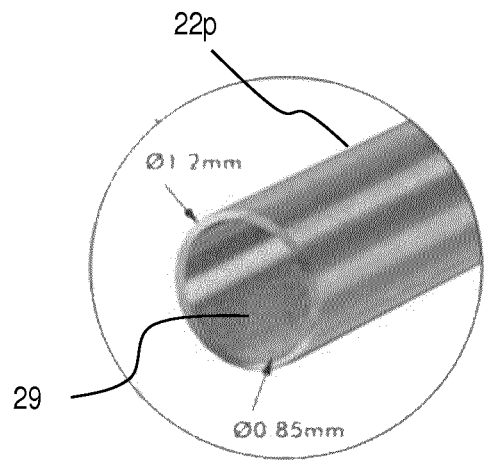
FIGS. 5A and 5B respectively show perspective, close-up views of the proximal and distal ends of the probe.
Figure 5B:
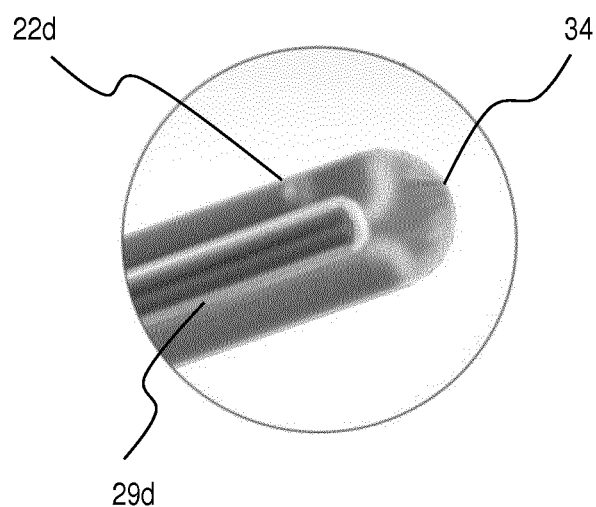

FIG. 4 shows an example of a single-wire surgical tool 20 according to an embodiment of the present invention. The single wire surgical tool 20 includes a probe 22 (having distal end 22d and proximal end 22p), the proximal end 22p of which is swaged to the proximal end 24d of a seton 24. Handle 26 is located on the probe 22, and is movable along the length (i.e. in a direction from the proximal end 22p to the distal end 22d, herein referred to as "back and forth") of the probe 22. The probe contains a single channel 29 (not shown in this drawing) which contains a stainless steel support wire 30 (also not shown, and herein just "wire"), which may be in the direction of the longitudinal axis of the probe, along the channel (herein referred to as "back and forth" motion), and may be completely retracted from the channel. At the proximal end 30p of the wire is a handle portion 32, which is used to effect this back and forth motion. FIGS. 5A and 5B respectively, show close-up views of the proximal end 22p and distal end 22d of the probe 22. In FIG. 5A, the channel 29, through which the wire 30 may pass. In the embodiments shown in the drawings, the probe is made from extruded isoplast 2530 TPU, though other materials may be used. The probe in this embodiment may also include a photoluminescent coating so that it may be more easily spotted upon emergence from the internal opening. In FIG. 5B, the distal end 22d of the probe 22 is shown. In order to minimize the risk of injury to the patient, the distal end 22d has a rounded shape, which in the present embodiment includes a hemispherical portion 34. The distal end 29d of the channel 29 is also shown, and can be seen to be narrower here than in FIG. 5A.

Figure 6A:
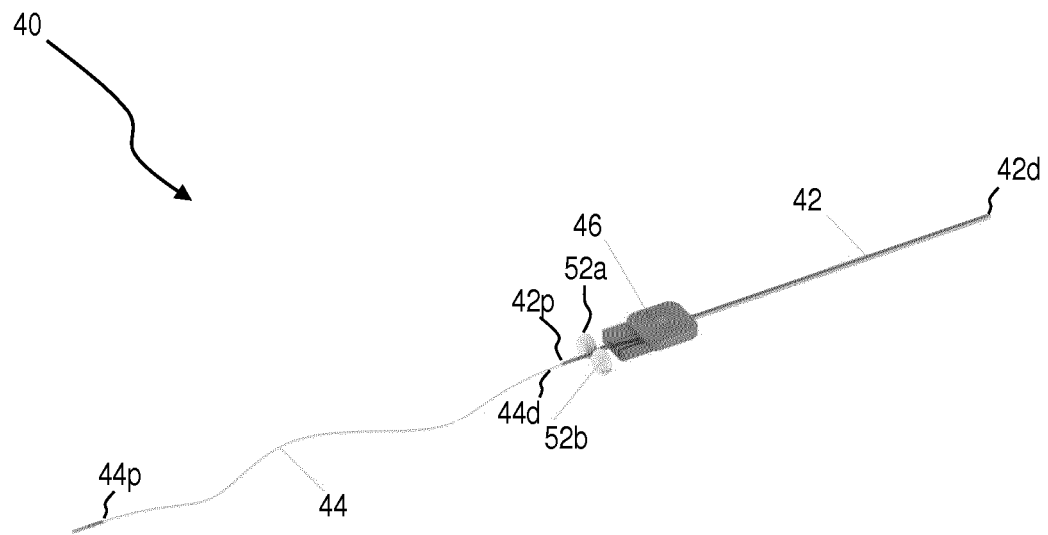
FIGS. 6A and 6B show perspective views of a surgical tool according to another embodiment of the present invention.
Figure 6B:
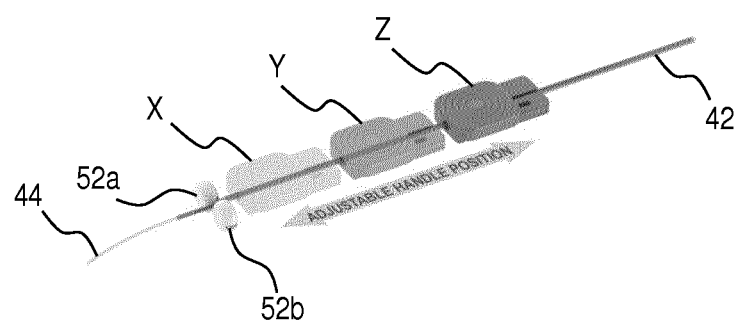

FIG. 6A shows an example of a multi-wire surgical tool 40 according to another embodiment of the present invention. The multi-wire surgical tool 40 includes a probe 42 (having distal end 42d and proximal end 42p), the proximal end 42p of which is swaged to the proximal end 44d of a seton 44. Handle 46 is located on the probe 42, and is movable along the length in a back and forth direction along the probe 42, as described above. FIG. 6B shows the handle 46 moving between three positions X, Y and Z on probe 44. Unlike in FIG. 4, the probe contains channels 49a and 49b, to accommodate stainless steel support wires 50a and 50b respectively, which are movable along and retractable from the proximal end of their respective channels. The movement of the wires 50a, 50b along the channels 49a, 49b may be effected by the handle portions 52a, 52b located at the distal ends of each wire 50a, 50b.

Figure 7A:
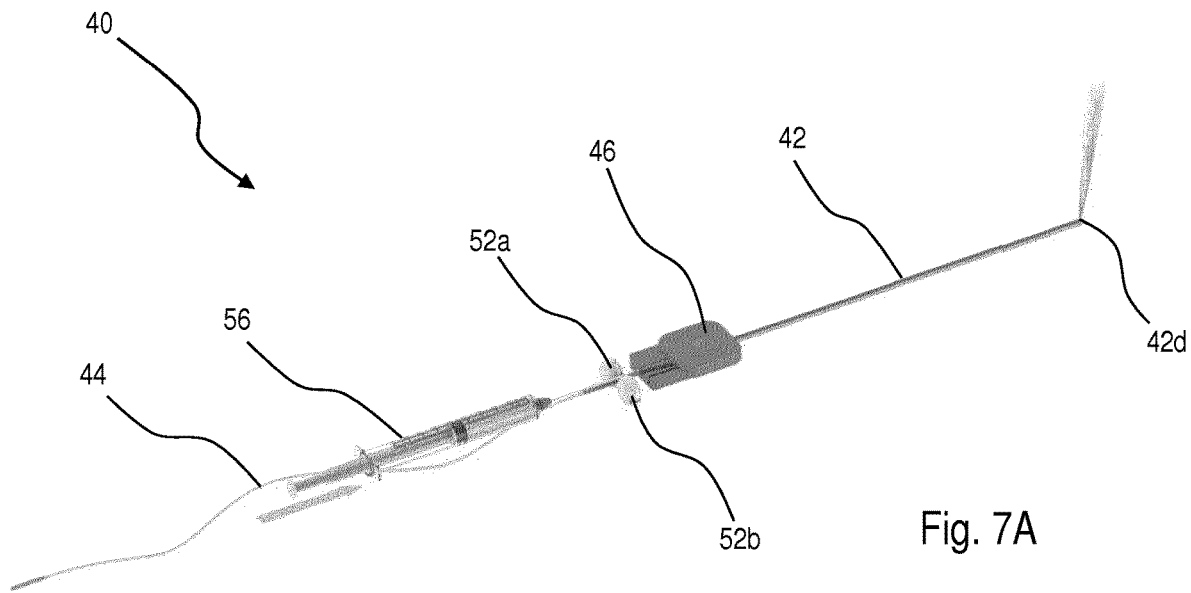
FIGS. 7A and 7B show perspective views of a surgical tool according to yet another embodiment of the present invention.

FIG. 7A shows a modified example 40' of the embodiment shown in FIG. 6, in which a liquid delivery channel 55 is also present in the probe 42. In use, hydrogen peroxide may be injected into liquid delivery channel 55 using a syringe 56. Liquid delivery channel 54 runs along the full length (i.e. from proximal end 42p to distal end 42d) of the probe 42, and terminates in aperture 58. When the probe 42 is in place inside a fistula tract (e.g. F, as shown in FIG. 2A), and has emerged into the anal canal from the internal opening (e.g. I, as shown in FIG. 1), the hydrogen peroxide is injected through the probe 42 so that the location of the internal opening may be pinpointed. In the present embodiment, the aperture 58 is located at a side of the hemispherical portion 54 of the distal end 42d of the probe 42, but in other embodiments, it may be located at the distal-most point of the probe 42. The aperture 58 is shown in closer detail in FIG. 7B.

Figure 7B:
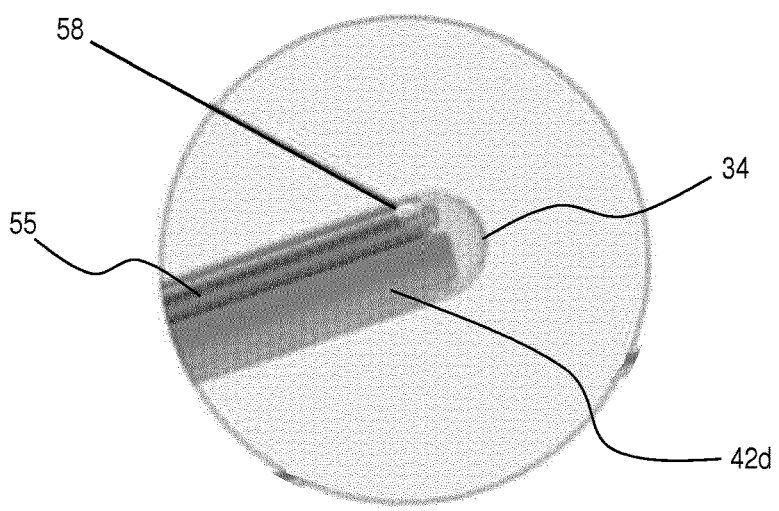
Figure 8A:
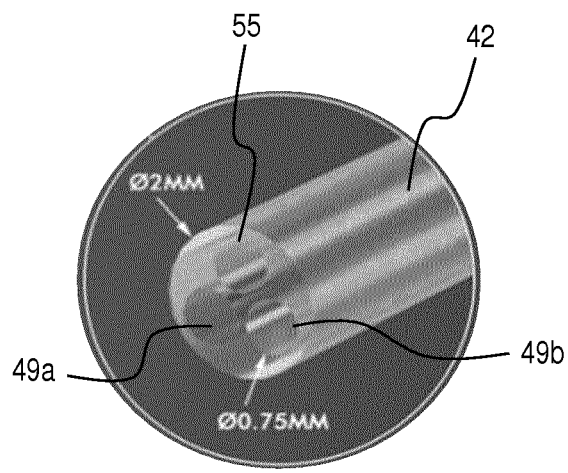
FIGS. 8A and 8B show perspective, close-up views of the internal channel structure of probes which may be used in embodiments of the present invention.
Figure 8B:
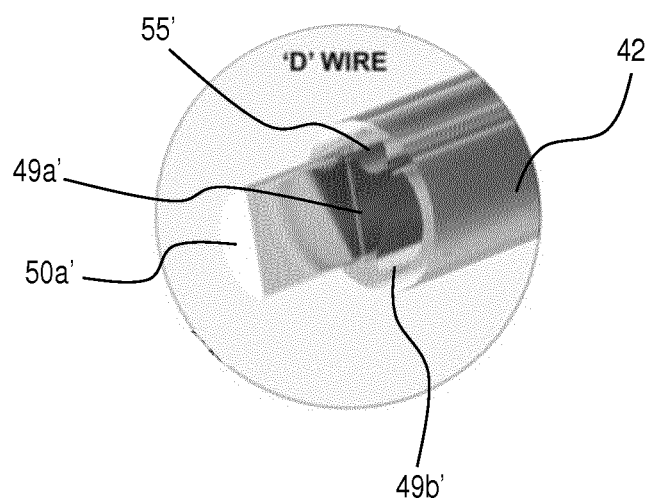

FIGS. 8A and 8B show more detailed versions of the internal channel structure of the embodiment shown in FIGS. 7A and 7B. In FIG. 8A, the channels 49a, 49b, and the liquid delivery channel 55 are all cylindrical channels, shown in (circular) cross section in the cutaway view of FIG. 8A. In examples such as this one, the wires are preferably also cylindrical, in order to ensure as flush a fit as possible into their respective channels 49a, 49b. In FIG. 8B, the channels 49a', 49b' are D-shaped, and are arranged to accommodate wires 50a', 50b' having a D-shaped cross section. Such wires have an increased rigidity, and provide improved torsional stability to the arrangement. As can be seen, the D-shaped channels 49a', 49b' are arranged with their straight sides facing other, and at an angle of approximately 20° from each other. This means that the liquid delivery channel 55' fits into the V-shaped gap between the two. It should be noted that in FIGS. 8A and 8B, the channels 49a, 49b, 55, 49a', 49b', 55' are formed in a solid probe, rather than inside a thin outer shell. Only the shells or surfaces are shown in the drawings in order to emphasize that the channels 49a, 49b, 55, 49a', 49b', 55' have length, and are not just holes or dents at an end surface.

Figure 9:
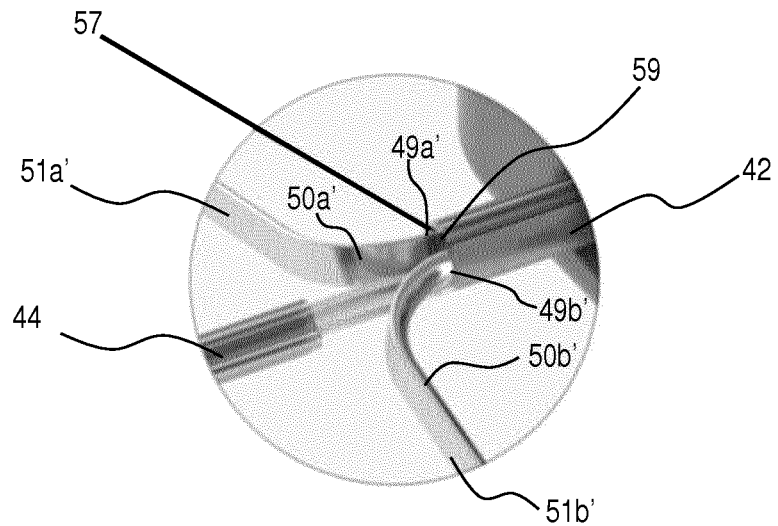
FIG. 9 shows a perspective view of the proximal end of the probe as depicted in FIG. 8B, with the D-shaped wires and seton in place.

FIG. 9 shows the proximal end 42p of the probe when the D-shaped wires 50a', 50b' are in place in channels 49a', 49b'. In FIG. 9 the wires 50a', 50b' are splayed outwards at 90° from the longitudinal axis of the probe 42. The arms 51a', 51b' are connected to the handle portions 52a, 52b as shown e.g. in FIG. 6. The proximal end of the liquid delivery channel 55' also forms an aperture 59 into which a syringe 56 or the like may be inserted to provide hydrogen peroxide or another liquid to the liquid delivery channel 55'. The distal end 44d of the seton 44 is also shown in FIG. 9, connected to an end surface 57 of the probe 42.

Figure 10A:
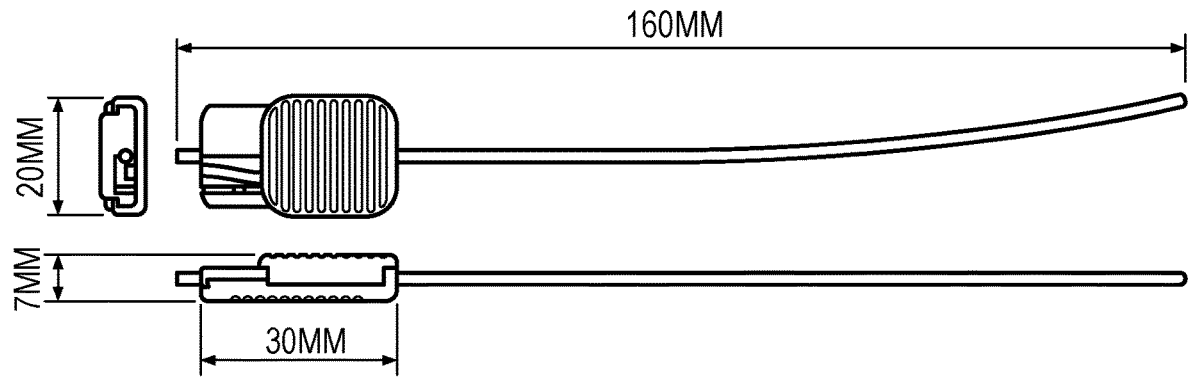
FIGS. 10A to 10O show various views of the handle (and how it may be used) located on the probe, which may be used in embodiments of the present invention.
Figure 10B:
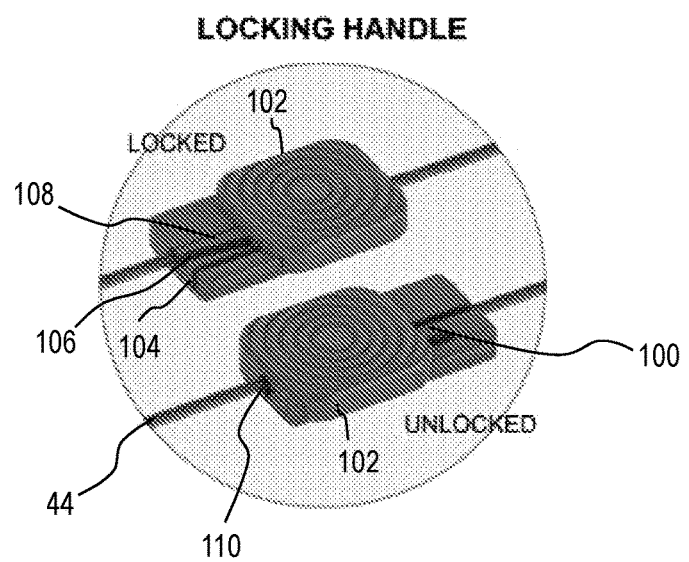

FIGS. 10A and 10B show some of the features of the handle 46 in more detail, though all of the description below relates equally well to handle 26. More specifically, FIG. 10A shows plan and side views of the handle 46, including the dimensions thereof in a preferred embodiment, and FIG. 10B illustrates the locking mechanism of the handle. Handle 46 includes a base 100, on which is mounted a sliding tab 102. On the underside of tab 102 is a projection (not shown), which is configured to fit inside guide channel 104, which is formed in the upper surface of base 100, and is parallel to the edges thereof. The guide channel 104 ensures that the tab 102 is only able to move in a direction which is parallel or substantially parallel to the back and forth direction defined above. Also formed in the surface of base 100 is a second, oblique channel 106, which defines a substantially triangular tongue 108, which is able to move slightly in a direction perpendicular to the guide channel 104. A second projection (also not shown) is formed on the underside of the tab 102, and rests within the oblique channel 106. Unlike the first projection, the second projection is able to flex slightly from side to side. The probe 42 rests in a probe channel 110, which is bounded on one side by a rigid surface of the base 100 and on the other side by a sidewall of the tongue 108.

Figure 10C:
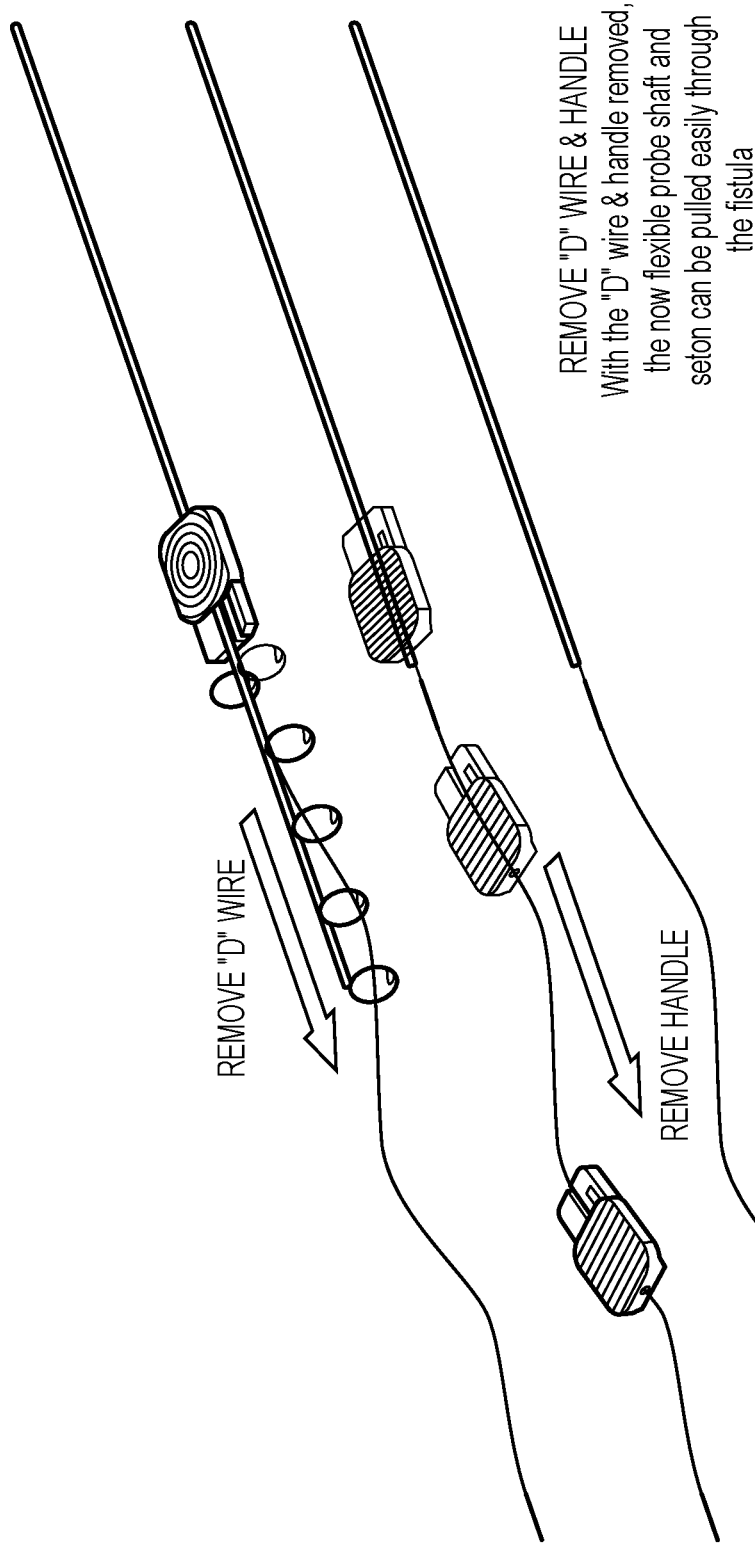

FIG. 10B shows that the tab is movable between a locked position and an unlocked position. The locking mechanism arises from a combination of the second projection and the side-to-side movement of the tongue 108. In the unlocked position, the tab 102 is located at a proximal end 46p of the handle 46. Here, the second projection rests in the oblique channel 106 in an unflexed position. However, when the tab 102 is moved from the proximal end 46p to the distal end 46d, it is forced to flex downwards (in the coordinates of the upper view in FIG. 10A), and thus exerts a force in the upward direction (again in the coordinates of the upper view in FIG. 10A) on the tongue 108. This upward force causes the sidewall of the tongue 108, which bounds the probe channel 110 to move upwards, causing it to pinch and grip the probe 42, preventing the handle 46 from moving back and forth along the probe 42. In the unlocked position, as shown in FIG. 11, the handle 46 is able to slide all the way along the probe 42, along the seton 44 (both of which pass through the probe channel 110 of the handle 46, which is not gripped by the tongue 108 when the tab 102 is in the unlocked position) and off of the proximal end 44p of the seton 44. In this way, once the probe 42 has been passed all the way through a fistula tract, using the handle 46 for improved control, the handle can be unlocked and removed, so that the seton 44 may be drawn through the fistula tract. FIG. 10C shows a process wherein first a wire e.g. 50a, then the handle 46 may be removed.

Figure 11A:
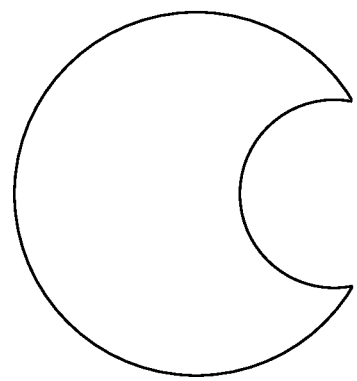
Figure 11B:
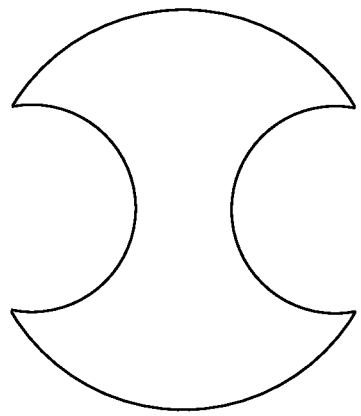
Figure 11C:
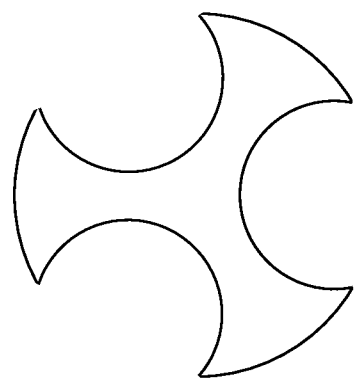

FIGS. 11A to K show possible cross sections for the setons 24, 44. In particular FIGS. 11A, B and C show setons which have a substantially circular cross section save for cutout sections. FIGS. 11A, B and C show seton cross sections with one, two and three cutout sections respectively, though it is possible to have four or more cutout sections in the cross section, to provide even more drainage. In the examples depicted, the cutout sections are arranged circumferentially evenly, though in other embodiments, this may not be the case.

Figure 11D:
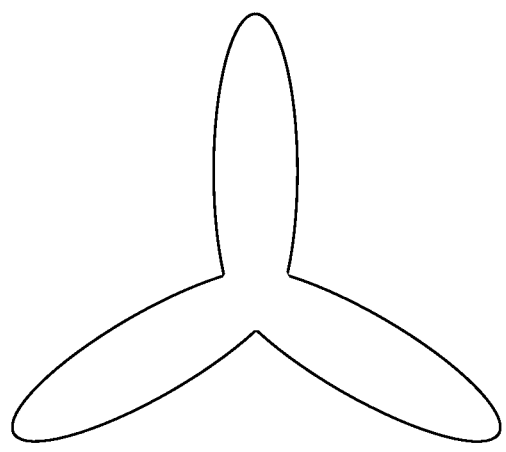
Figure 11E:
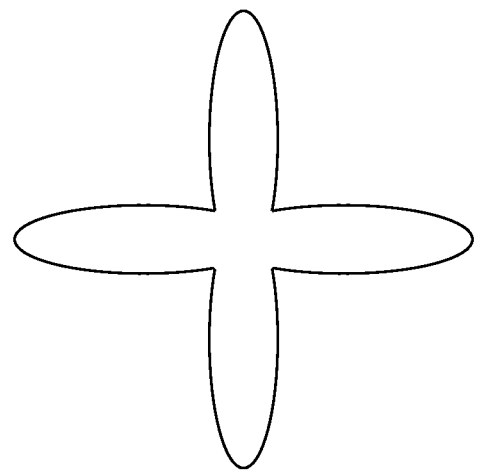
Figure 11F:
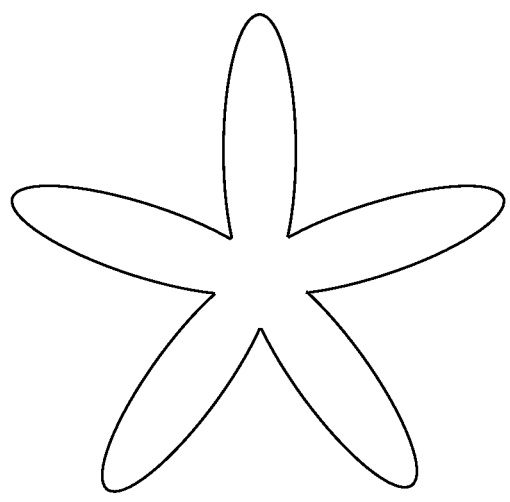
Figure 11G:
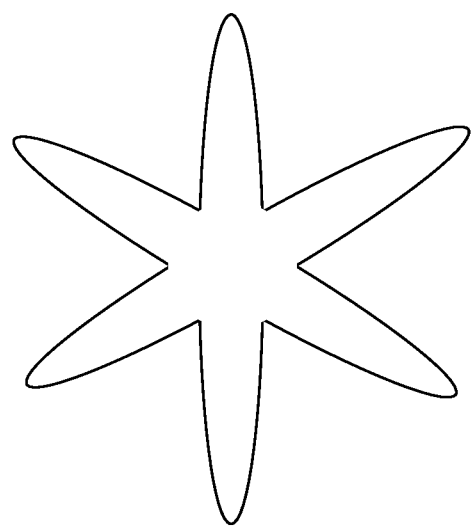

FIGS. 11D, E, F and G show cross sections having a plurality of radial arms. Again, as with the cutout sections described in the previous paragraph, the radial arms are arranged circumferentially evenly, but this may not be the case in alternative embodiments (not shown). A perspective view of the four-armed structure, or cross-shaped cross section is shown in FIG. 12B.

Figure 11H:
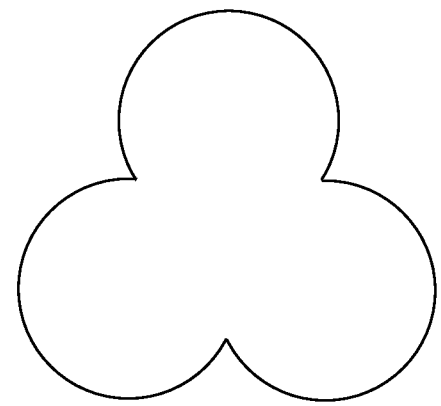
Figure 11J:
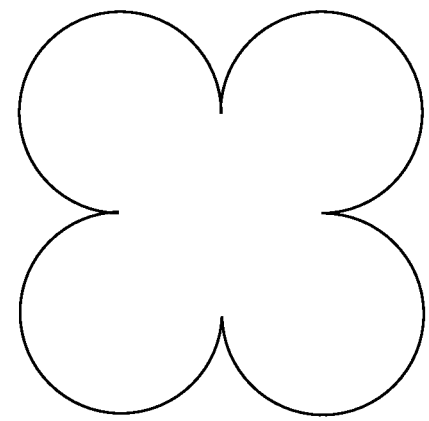
Figure 11K:
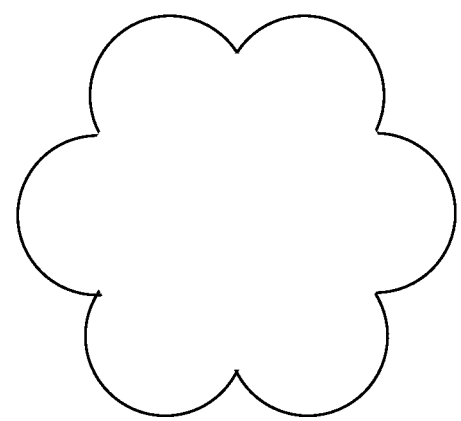

FIGS. 11H, J and K show cross sections having lobe-shaped arms. FIG. 11H has three lobes and may be referred to as e.g. clover-shaped, or club-shaped; FIG. 11J may be referred to as e.g. clover-shaped or shamrock-shaped; FIG. 11K has six lobes. Though not shown, embodiments having five lobes, or more than six lobes are also envisaged. Cross sections shaped like these may also be referred to as flower-like cross sections (regardless of the number of lobes).

Figure 12A:
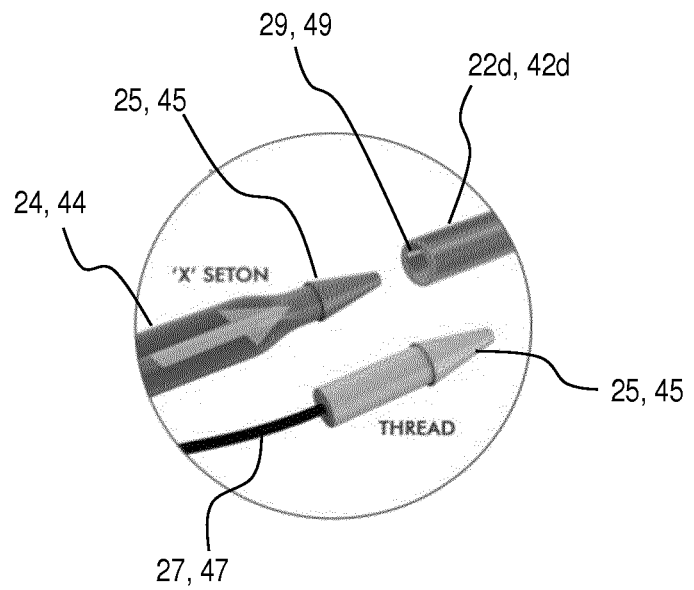
FIGS. 12A and 12B show perspective, close-up views of the distal and proximal end of a seton which may be used in embodiments of the present invention.
Figure 12B:
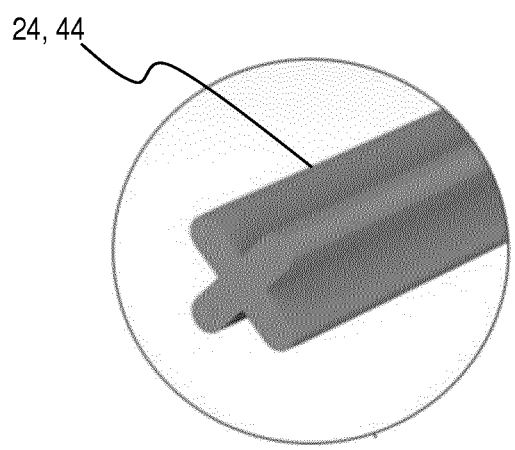

FIG. 12A shows an example of an alternative connection between the distal end 24d, 44d of the seton 24, 44 and the proximal end 22d, 42d of the probe 22, 42. In this embodiment, rather than swaging the seton 24, 44 and probe 22, 42 together, the proximal end 24d, 44d of the seton has a pointed tip 25, 45, which is configured to fit snugly inside a channel 29, 49 of the probe 22, 42. The pointed tip 25, 45 (though not shown in the present drawings) may have a raised ring which is configured to cooperate with a circumferential recess on the inner surface of the channel 29, 49 to provide a "snap-fit" connection for a more secure fit. Conversely, the recess may be on the pointed tip 25, 45 and the raised ridge may be on the inner surface of the channel 29, 49. As is also shown in FIG. 12A, the channel 29 need not only be used with a seton as described throughout this application. Alternatively, as shown, a regular thread 27, 47 may be used in place of the seton 24, 44, to the same effect. A pointed tip 25, 45 may be fitted at the distal end 27d, 47d of said thread 27, 47.

Figure 13:
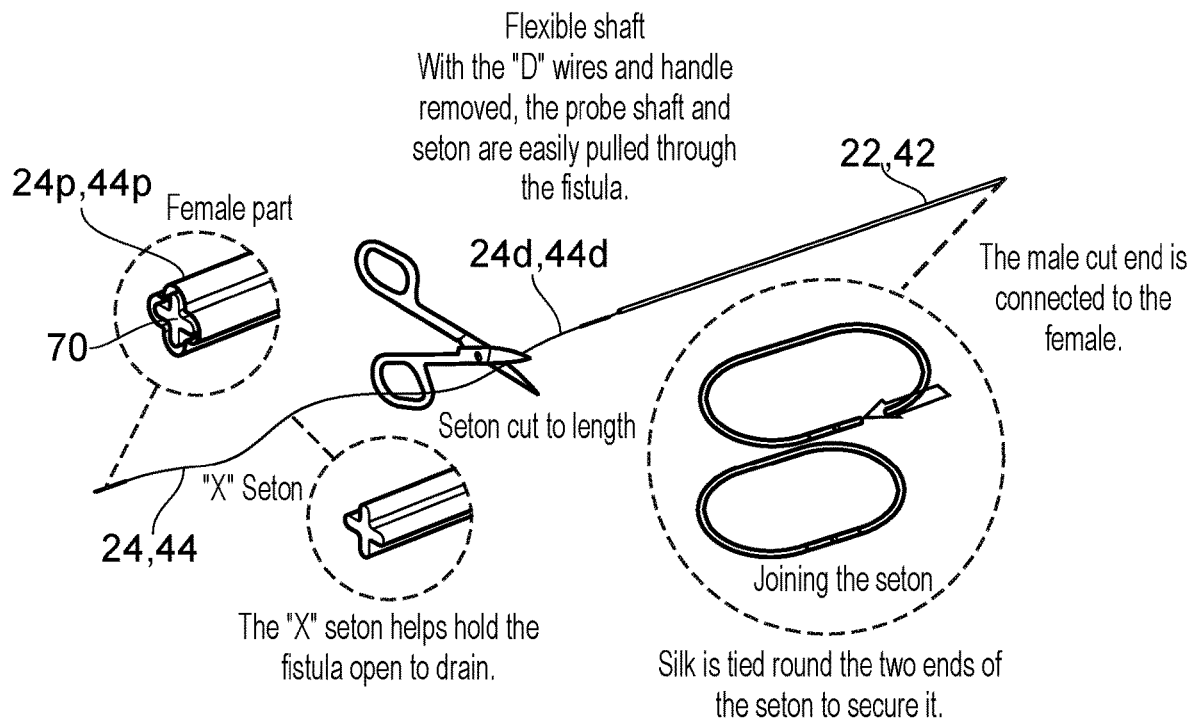
FIGS. 13 and 14 show ways of joining the ends of the seton once it has been drawn through the fistula tract (the tract not shown).
Figure 14:
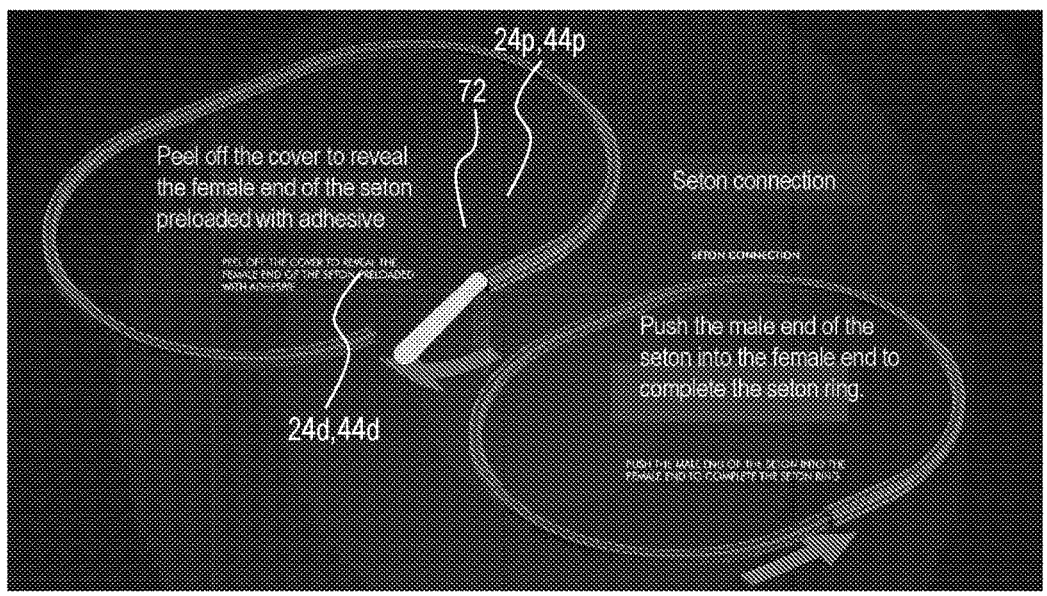

FIG. 13 shows how the ends of the seton 24, 44 may be joined after drawing through the fistula tract. In the embodiment shown, the proximal end 24d, 44d is a female end, containing a recess 70. In this embodiment, the seton 24, 44 has a four-lobed flower like cross section. After insertion the seton 24, 44 is cut at its distal end 24d, 44d from the proximal end 22p, 42p of the probe 22, 42. The probe 22, 42 and the remainder of the seton 24, 44 may then be discarded. The distal end 24d, 44d of the cut seton 24, 44 represents a male end having a shape corresponding to the recess 70. To join the ends, the male end is inserted into the female end. Then, optionally silk may be tied around the join, in order to secure it. FIG. 14 shows an embodiment wherein the proximal end 24p, 44p of the seton 24, 44 is first covered in with a tab 72 in order to protect an adhesive which is preloaded in the female end, to provide a stronger join upon insertion of the male end. As mentioned earlier in the application, the adhesive may be a UV-curable adhesive.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A surgical tool for use in the treatment of anal fistulas, the tool including:
    an elongate, flexible probe having a channel running therethrough;
    a seton attached to a proximal end of the probe;
    a wire located within the channel, and movable along the channel;
    wherein the probe has a first stiffness and the wire has a second stiffness, the first stiffness being less than the second stiffness; and wherein the probe further includes a liquid delivery channel, arranged to receive liquid at a proximal end, and which terminates in an aperture at its distal end, the liquid delivery channel arranged, in use, to deliver liquid to a region surrounding the distal end of the probe.

2. The surgical tool according to claim 1, wherein the wire is fully retractable from the channel.

3. The surgical tool according to claim 1, wherein a distal end of the probe is rounded.

4. The surgical tool according to claim 1, wherein a proximal end of the wire includes a handle portion.

5. The surgical tool according to claim 1, wherein the probe further comprises a photoluminescent material.

6. The surgical tool according to claim 1, wherein the length of the probe is no less than 3 cm and no more than 20 cm.

7. The surgical tool according to claim 1, wherein the outer diameter of the probe is no more than 5 mm.

8. The surgical tool according to claim 1, further including a handle located at or near the proximal end of the probe.

9. The surgical tool according to claim 8, wherein the handle is movable along the probe.

10. The surgical tool according to claim 8, wherein the handle is removably attached to the probe.

11. The surgical tool according to claim 8, wherein the handle includes a locking mechanism for locking the handle at a selected position along the probe.

12. The surgical tool according to claim 11, wherein the locking mechanism includes an actuation means which is movable between a locked position and an unlocked position.

13. The surgical tool according to claim 1, wherein the wire is curved in shape.

14. The surgical tool according to claim 1, wherein the wire is deformable to the extent that it is able to hold its shape after deformation into a given configuration.

15. The surgical tool according to claim 1, wherein a cross section of the seton is shaped such that, when the seton is in place inside a fistula tract, not all of the perimeter or circumference of the cross section is in contact with a wall of the fistula tract.

16. The surgical tool according to claim 15, wherein the cross section of the seton is circular, substantially circular, elliptical or substantially circular, or substantially elliptical, and includes a cutout portion.

17. The surgical tool according to claim 1, wherein the seton has cooperating proximal and distal ends.

18. A surgical tool for use in the treatment of anal fistulas, the tool including:
    an elongate, flexible probe having a channel running therethrough;
    a seton attached to a proximal end of the probe;
    a wire located within the channel, and movable along the channel;
    wherein the probe has a first stiffness and the wire has a second stiffness, the first stiffness being less than the second stiffness; and
    wherein the wire is a first wire having the second stiffness, and further including a second wire having a third stiffness.

19. The surgical tool according to claim 18, wherein the probe includes:
    a first channel, and
    a second channel, and
    the first wire is located inside, and is movable along the first channel; and
    the second wire is located inside and is movable along the second channel.

20. The surgical tool according to claim 19, wherein one or both of the first channel and the second channel have a D-shaped, or substantially D-shaped cross section.

21. The surgical tool according to claim 18, wherein one or both of the first wire and the second wire have a D-shaped, or substantially D-shaped cross section.

22. A surgical tool for use in the treatment of anal fistulas, the tool including:
    an elongate, flexible probe having a channel running therethrough;
    a seton attached to a proximal end of the probe;
    a wire located within the channel, and movable along the channel;
    wherein the probe has a first stiffness and the wire has a second stiffness, the first stiffness being less than the second stiffness;
    wherein a cross section of the seton is shaped such that, when the seton is in place inside a fistula tract, not all of the perimeter or circumference of the cross section is in contact with a wall of the fistula tract; and
    wherein either:
        (a) a cross section of the seton includes a plurality of radial arms;
        (b) a cross section of the seton includes a plurality of radial lobes; or
        (c) a cross section of the seton is flower-shaped, clover-shaped, club-shaped or shamrock-shaped.

23. A surgical tool for use in the treatment of anal fistulas, the tool including:
    an elongate, flexible probe having a channel running therethrough;
    a seton attached to a proximal end of the probe;
    a wire located within the channel, and movable along the channel;
    wherein the probe has a first stiffness and the wire has a second stiffness, the first stiffness being less than the second stiffness;
    wherein the seton has cooperating proximal and distal ends; and
    wherein one of the proximal end and the distal end of the seton has a projection, or forms a projection, and the other of the proximal end and the distal end of the seton has a recess configured to receive said projection.

24. The surgical tool according to claim 23, wherein the proximal end of the seton has the recess, and the distal end of the seton has or forms the projection.

25. A surgical tool for use in the treatment of anal fistulas, the tool including:
    an elongate, flexible probe having a channel running therethrough;
    a seton attached to a proximal end of the probe;
    a wire located within the channel, and movable along the channel;
    wherein the probe has a first stiffness and the wire has a second stiffness, the first stiffness being less than the second stiffness;
    wherein the seton has cooperating proximal and distal ends; and
    wherein one of the proximal end or distal end of the seton includes an adhesive.

* * * * *